United States Patent [19]
Clawson

[11] Patent Number: 5,149,324
[45] Date of Patent: Sep. 22, 1992

[54] SURGICAL NEEDLE WITH REMOVABLE HUB

[75] Inventor: Benjamin S. Clawson, Oakland, Calif.

[73] Assignee: Surgical Dynamics, Inc., Alameda, Calif.

[21] Appl. No.: 516,108

[22] Filed: Apr. 27, 1990

[51] Int. Cl.⁵ ............................................... A61M 5/50
[52] U.S. Cl. .................................... 604/110; 604/240; 604/164
[58] Field of Search ............... 604/110, 158, 161, 164, 604/165, 239, 240, 242, 243, 272

[56] References Cited

U.S. PATENT DOCUMENTS

| | | | |
|---|---|---|---|
| 2,517,689 | 8/1950 | Lement | 604/243 X |
| 2,855,927 | 10/1958 | Henderson | 604/243 X |
| 3,035,616 | 5/1962 | Hamilton | 604/243 X |
| 3,372,697 | 3/1968 | Keller | 604/243 X |
| 3,472,227 | 10/1969 | Burke | 604/243 |
| 3,523,531 | 8/1970 | Burke | 604/272 |
| 3,523,533 | 8/1970 | Burke | 604/240 |
| 4,187,848 | 2/1980 | Taylor | 604/243 |
| 4,944,723 | 7/1990 | Haber et al. | 604/110 |

FOREIGN PATENT DOCUMENTS 0191122  8/1986  European Pat. Off. ............ 604/240

Primary Examiner—John D. Yasko
Assistant Examiner—Adam J. Cermak
Attorney, Agent, or Firm—Fliesler, Dubb, Meyer and Lovejoy

[57] ABSTRACT

A surgical needle 20 includes a needle body 26 which is secured onto a hub body 24. The hub body 24 is irreversibly removable from the needle body 26 in order for the needle body 26 to be used as a trocar. The hub body 24, being irreversibly disconnectable from the needle body 26, ensures that the hub body 24 cannot be reconnected to the needle body 26 so that the surgical needle 20 cannot be used again.

4 Claims, 9 Drawing Sheets

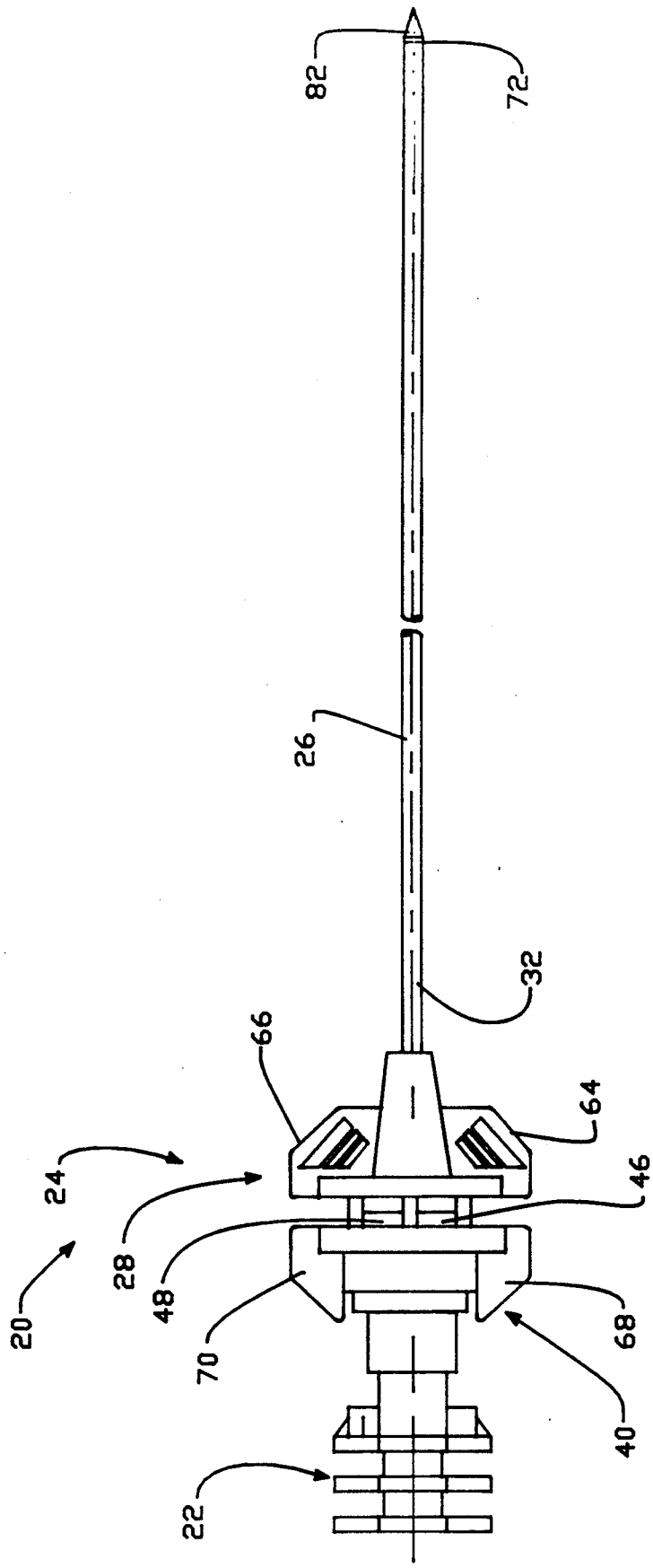

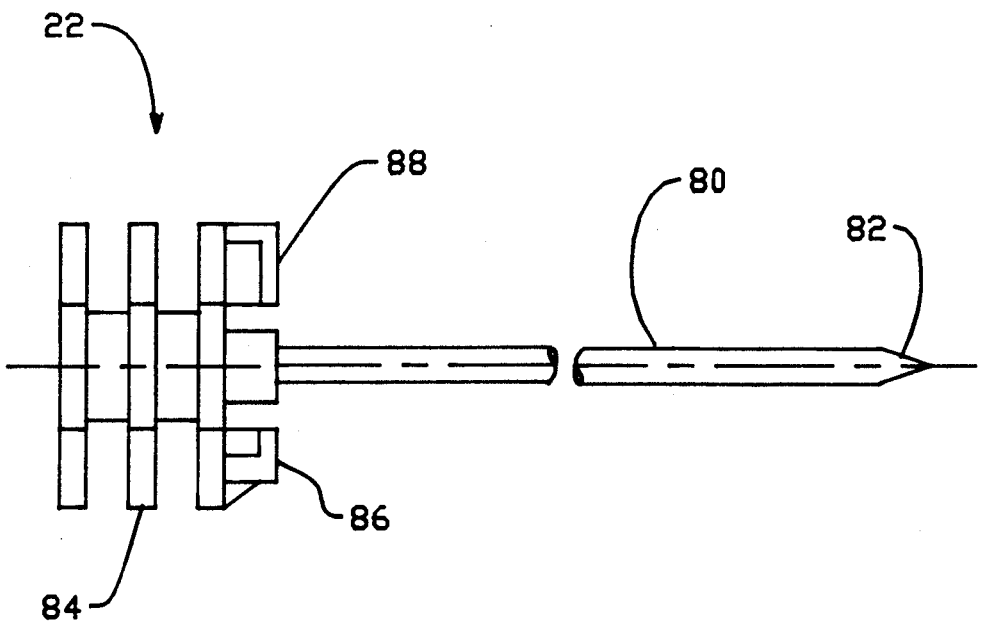
FIG.—3A
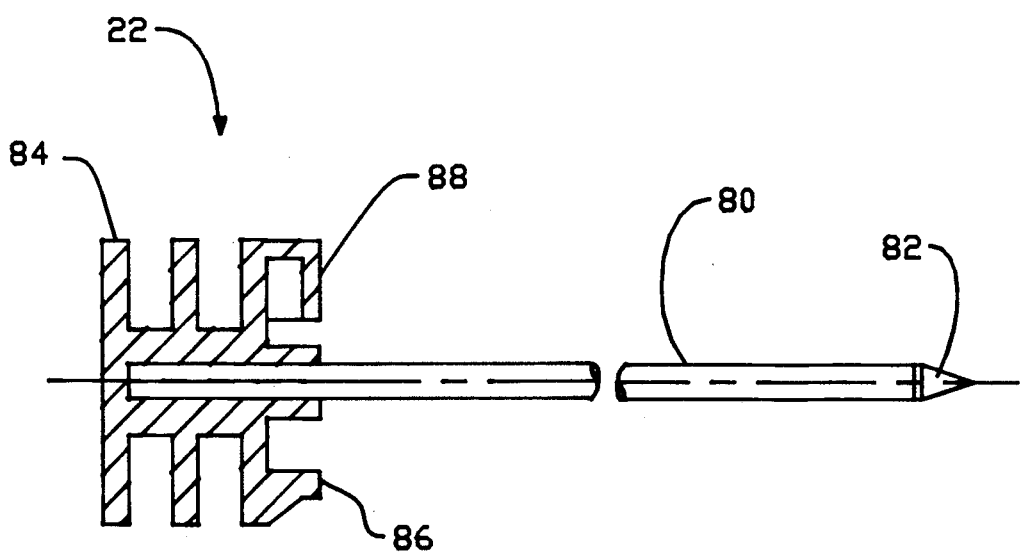
FIG.—3B

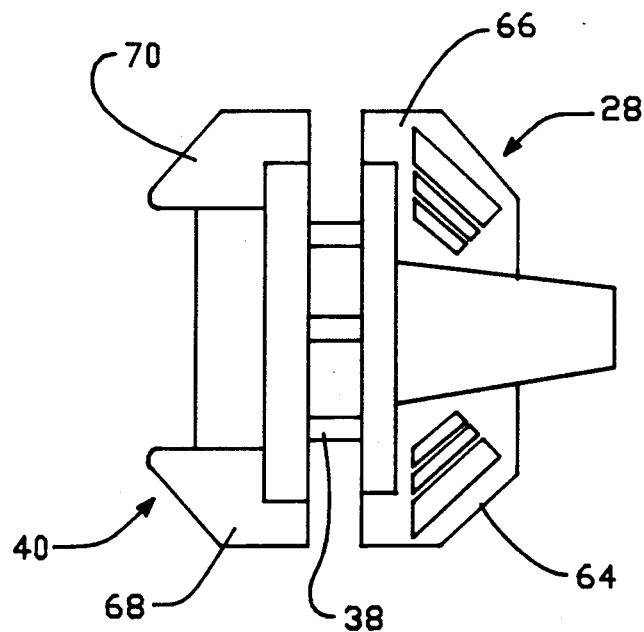
FIG.—4A
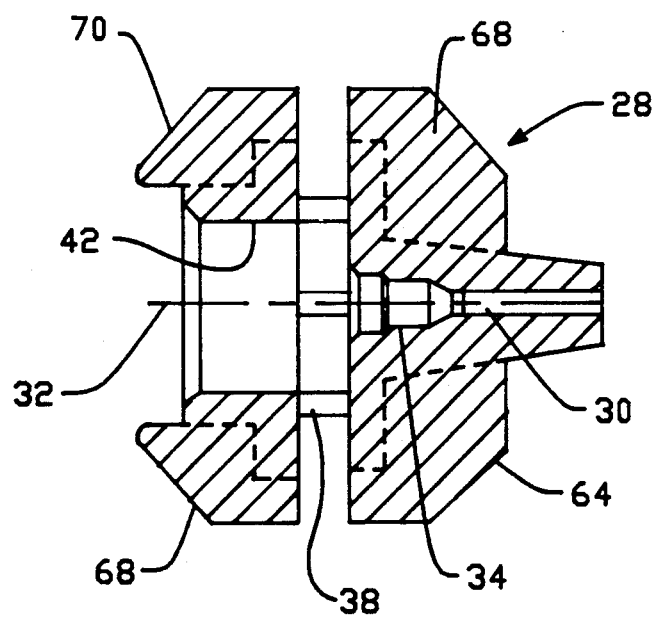
FIG.—4B

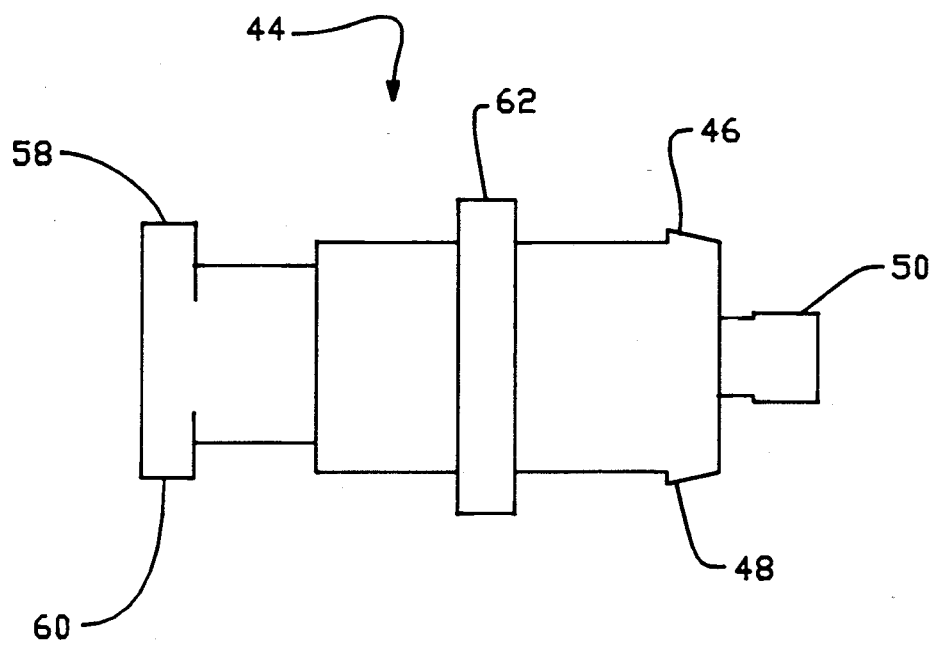
FIG.—5A
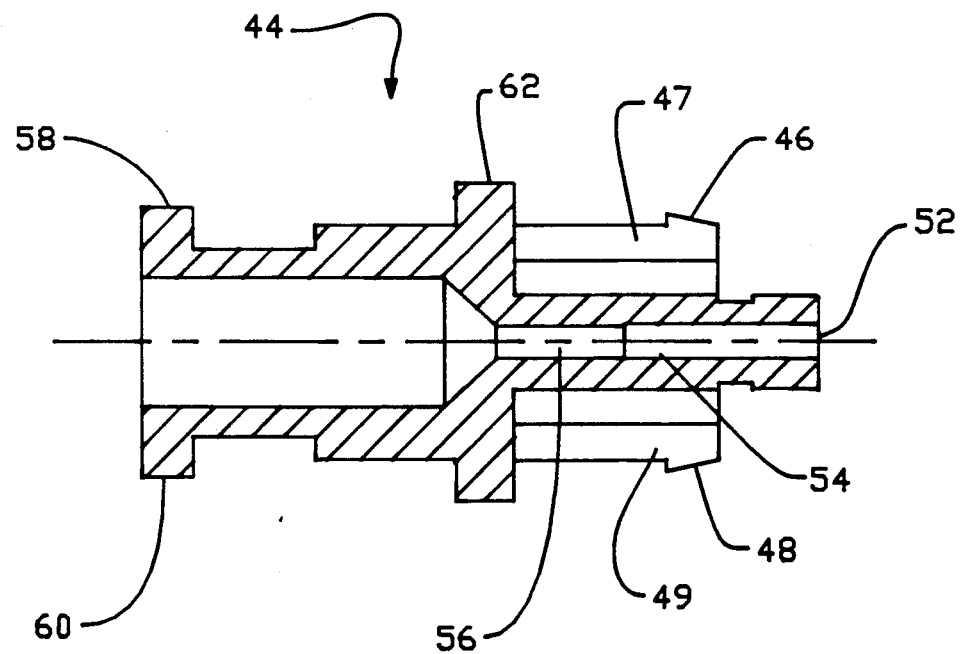
FIG.—5B

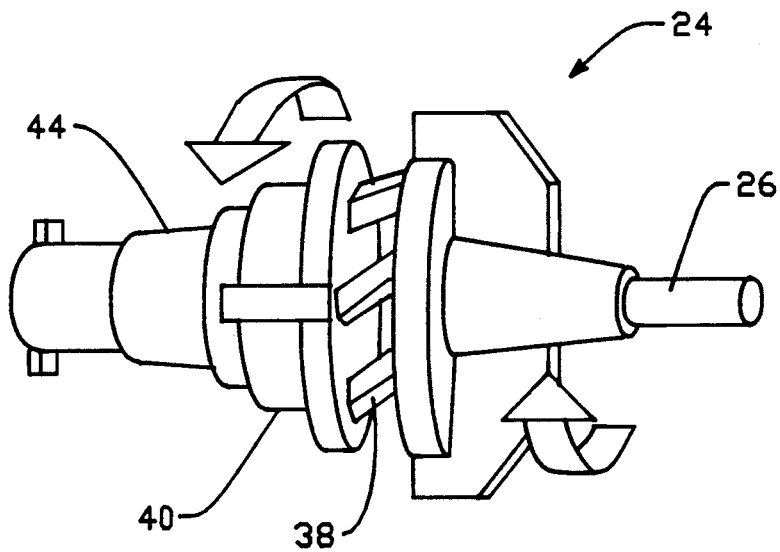
FIG.—6
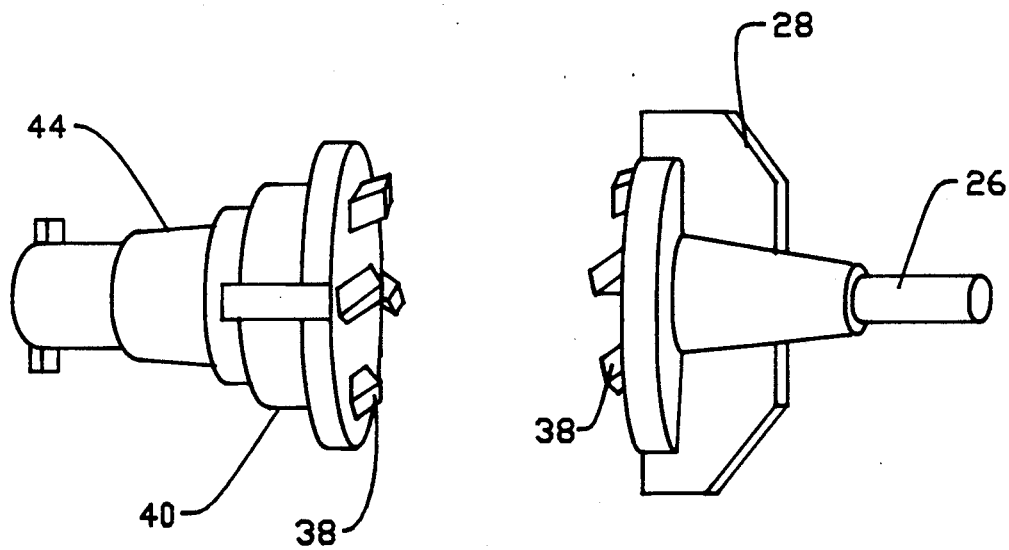
FIG.—7A  FIG.—7B

SURGICAL NEEDLE WITH REMOVABLE HUB

FIELD OF THE INVENTION

The present invention is directed to a surgical needle with a removable hub for use initially as a needle for the delivery of a fluid and subsequently with the hub removed as a trocar for guiding the insertion of other surgical instrumentation.

BACKGROUND OF THE INVENTION

The present invention is intended to be used with instrumentation which is disclosed in U.S. Pat. No. 4,863,430 entitled "INTRODUCTION SET WITH FLEXIBLE TROCAR WITH CURVED CANNULA" issued on Sep. 5, 1989 and U.S. Pat. No. 4,678,459 entitled "IRRIGATING, CUTTING AND ASPIRATING SYSTEM FOR PERCUTANEOUS SURGERY" issued on Jul. 7, 1987, both patents being incorporated herein by reference. Essentially, the introduction set includes a trocar which is initially introduced and used to guide a cannula to a position adjacent a surgical site. Once this is accomplished, the system for percutaneous surgery can be introduced through the cannula and the surgical procedure performed.

Often times before a surgical procedure is performed, certain diagnostic procedures are used to evaluate the surgical site to determine the advisability of the surgical procedure. For example, there is currently available on the market a surgical needle with a removable hub, which surgical needle can be used for directing a diagnostic fluid to a potential surgical site. If subsequent radiological images indicate that surgery is appropriate, the hub of the needle can be removed so that the needle can act as a trocar in order to guide other instrumentation to the surgical site. In this prior device, the hub is comprised of at least two portions which can be screwed together in order to compress an o-ring which holds the hub fixed relative to the needle. Once the two components of the hub are unscrewed, the O-ring is released, allowing the pieces to be slid off of the needle so that the needle can then be used as a trocar. With such an arrangement, it is possible that the hub could be reassembled onto the needle and the needle reused. Such reuse is often times not recommended or advisable and poses a disadvantage to this apparatus.

SUMMARY OF THE INVENTION

The present invention is directed to overcoming the disadvantages of the prior devices.

Accordingly, it is an object of the present invention to provide a needle which has a hub which can be removed from the needle if desired and not resecured to the needle once the hub has removed.

It is a further object of the present invention to provide a hub which requires that a portion of the hub be broken in order to remove the hub from the needle so that the hub cannot be resecured to the needle.

It is yet another object of the present invention to provide a hub whereby the hub can be assembled onto the needle with motion occurring along the longitudinal axis of the needle and whereby the hub can be removed from the needle by twisting or rotating the hub about the longitudinal axis of the needle. Thus, the hub can be removed with a simple process which does not apply any substantial force or motion along the longitudinal axis which might potentially alter the position of the needle.

It is yet another object of the present invention to provide for a hub which has connectors which are easily broken in order to remove the hub from the needle.

It is yet another object of the present invention to provide for a hub which applies compressive forces in order to secure the needle to the hub and which relieves the compressive forces by irreversibly severing portions of the hub so that the hub can be removed from the needle.

Accordingly, the present invention includes a surgical needle having a needle body and a hub, which hub includes a device for securing the hub onto the needle body. The hub further includes a non-reusable connecting device for releasing the securing device in order to allow the hub to be removed from the needle body, which non-reusable connecting device does not allow the securing device to resecure the hub onto the needle body.

In another aspect of the invention, the surgical needle includes a needle body and a hub with a hub body, wherein the hub body defines a channel for receiving the needle body. The surgical needle further includes a first securing device for securing the needle body into the channel and a second securing device for cooperating with the first securing device for securing the needle body into the channel. The hub defines a device for lockingly receiving the second securing device. Further, the needle includes a device for connecting the lockingly receiving device to said hub body, which connecting device can be non-reconnectably severed to separate the hub body from the lockingly receiving device, with the second securing device received in the lockingly receiving device. in order to release the hub body from the needle body.

BRIEF DESCRIPTION OF THE FIGURES

FIG. 1A depicts an embodiment of the surgical needle of the invention with a stylet inserted therein.

FIG. 3A depicts the stylet of an embodiment of the invention as depicted in FIG. 1.

FIG. 3B depicts a cross-sectional view of the stylet of FIG. 3A.

FIG. 4A depicts a side view of a portion of the hub of the invention as shown in FIG. 1.

FIG. 4B depicts a cross-sectional view of the hub of FIG. 4A.

FIG. 5A depicts a side view of another portion of the hub of the invention as shown in FIG. 1.

FIG. 5B depicts a cross-sectional view of the hub of FIG. 5A.

FIG. 6 depicts a perspective view of the hub of the invention with a twisting motion applied thereto for removing the hub from the needle body.

FIG. 7 depicts a hub severed into two portions.

DETAILED DESCRIPTION OF THE PREFERRED EMBODIMENT

Figure 1B:
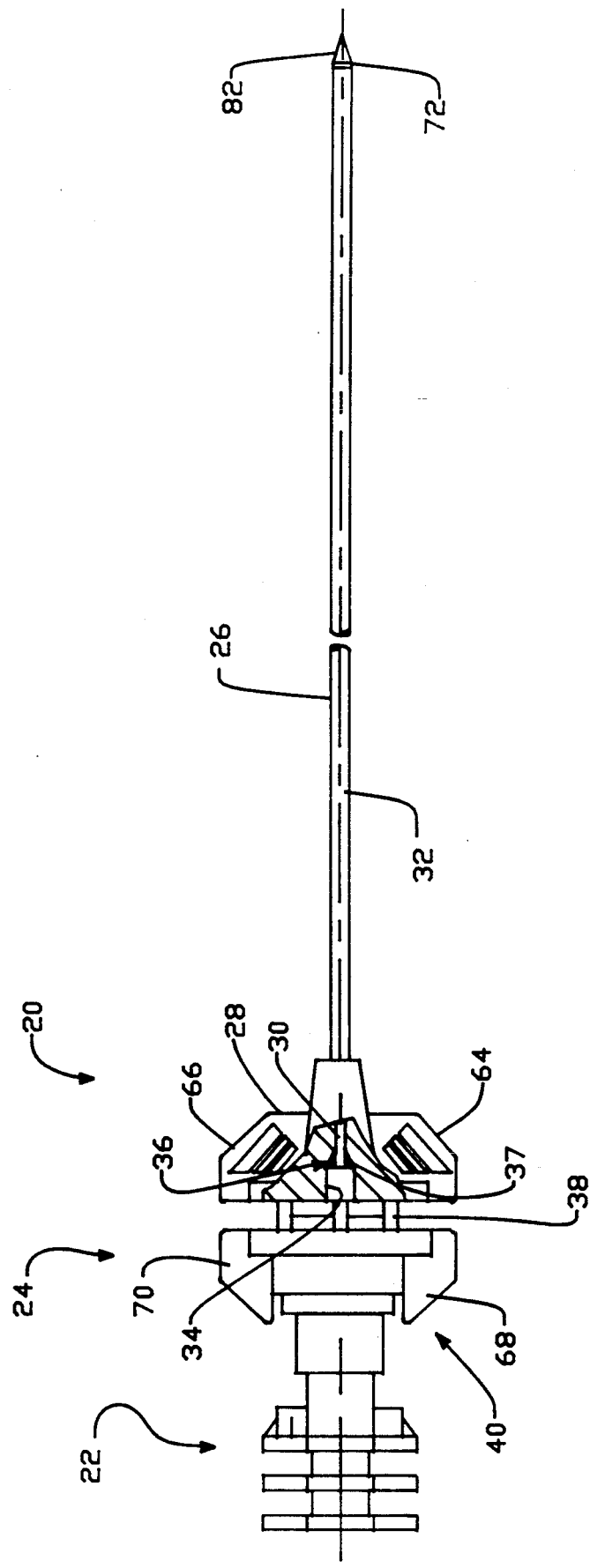
FIG. 1B depicts the embodiments of FIG. 1A with a portion thereof partially broken away and sectioned.
Figure 2:
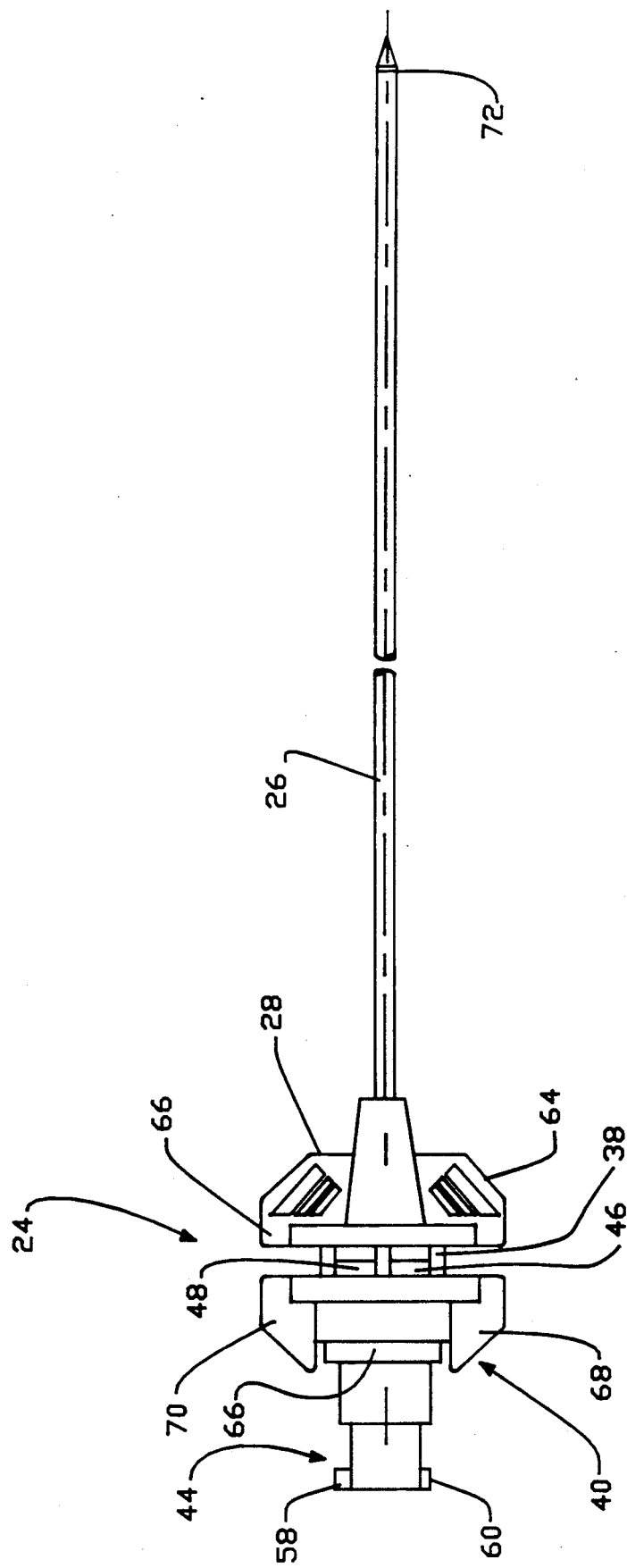
FIG. 2 depicts a surgical needle of the invention as depicted in FIG. 1.

With reference to the figures and in particular to FIG. 1, a surgical needle of the invention is depicted and identified by the number 20. Inserted through and connected to surgical needle 20 is a stylet 22. Surgical needle 20 includes a hub 24 from which extends a cylindrical hollow needle body 26. Hub 24 includes a hub body 28 which defines a cylindrical channel 30 (FIG. 1B, 4B) which receives the needle body 26. Needle body 26 defines a longitudinal axis 32 which is co-linear with the axis of the channel 30. The hub body 28 further defines a second cylindrical channel 34 which has an axis co-linear with the longitudinal axis 32. The second cylindrical channel 34 has a larger diameter than the first cylindrical channel 30 and is designed to receive an elastic O-ring 36 in such manner that the end 37 of the needle body 26 extends through the center of the o-ring 36.

The hub 24 further defines a plurality of substantially rectangular connecting fins 38 which connect a retention and looking ring 40 to the hub body 28. The retention and locking ring 40 includes a central port 42 which has an axis which is substantially co-linear with the longitudinal axis 32 of the needle body 26. The hub further defines a needle securing body 44 (FIG. 5A, 5B), which has somewhat flexible tabs 46, 48 which are spaced apart by slots 47, 49, and projection 50. Projection 50 defines a central bore 52 which has a first section 54 with a diameter which is slightly larger than the diameter of the needle body 28, and a second section 56 which has a diameter slightly smaller than the diameter of the needle body 26. Extending from an end of needle securing body 44, which is located distally from the projection 50, are third and fourth tabs 58, 60.

The needle securing body 44 can be inserted through the retention and locking ring 40 of the hub 24 until the first and second tabs 46, 48 snappingly lock the needle securing body 44 into position in the retention and locking ring 40. It is to be understood that the diameter of a peripheral edge of the first and second tabs 46, 48 and the diameter of a stop 62 of the needle securing body 44 are larger than the diameter of the central port 42 so that the needle securing body 44 becomes locked onto the retention and locking ring 40. As this occurs, the projection 50 is urged against and compresses the o-ring 36 so as to apply compressive forces to both the hub body 28 and the needle body 26, removably securing and positioning the needle body 26 onto the hub body 28. The first section 54 of the bore 52 receives the end of the needle body 26 and the second section 56 of the bore 52 acts as a stop to prevent the movement of the needle body 26 through the bore 52.

From the above, it can be ascertained that the assembly and securing of the needle body 26 relative to the hub 24 is accomplished along the longitudinal axis of the needle body 26.

In order to remove the hub 24 from the needle body 26, the flanges 64, 66 on the hub body 28 and the flanges 68, 70 on the retention and locking ring 40 can be engaged by the surgeon in order to place counter directional twisting motions on the hub body 26 and the retention and locking ring 40 about the longitudinal axis 32. This twisting or rotational motion causes the connecting fins 38 to break releasing the retention and locking ring 40 from the hub body 24 (FIGS. 6, 7A, 7B). As the retention and locking ring 40 is released, the projection 50 of the needle securing body 44 can no longer exert a compressive force on the o-ring 36 and thus can no longer securely position the needle body 26 relative to the hub body 28. This being the case, the hub body 28 can be easily slid, along the longitudinal axis 32, off of the needle body 26.

Thus, such an arrangement allows the needle body to be securely positioned relative to the hub and allows the hub to be easily removed from the needle body as desired.

Figure 8:
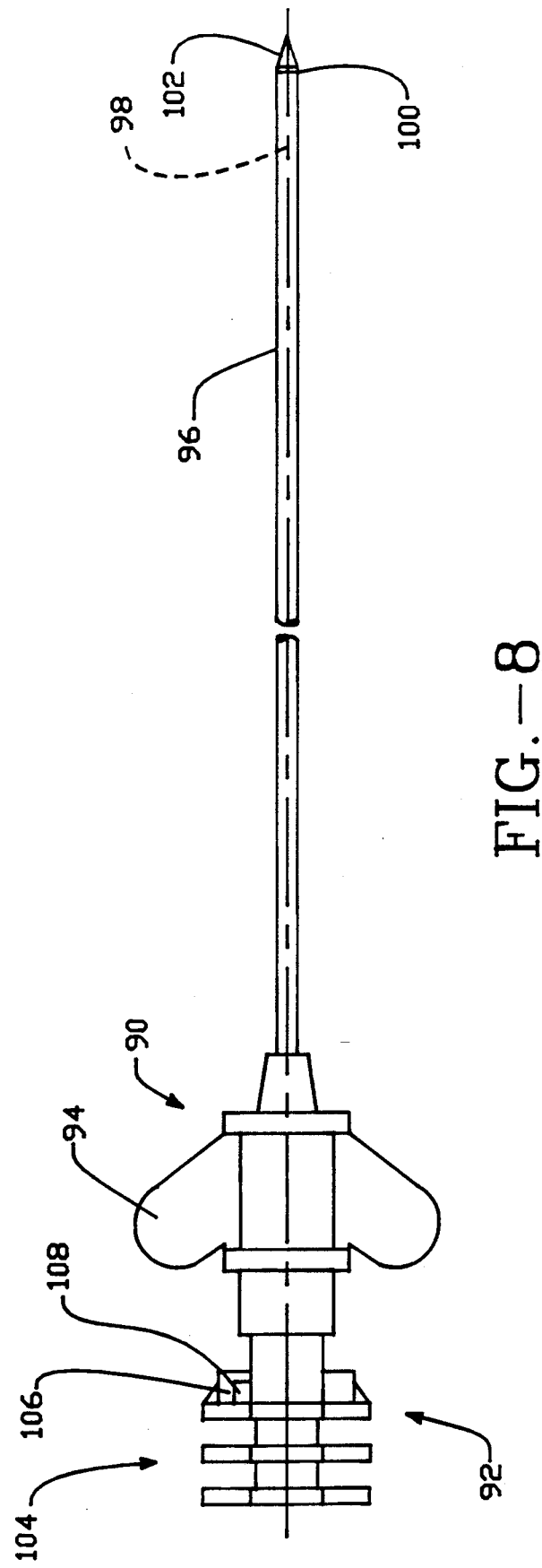
FIG. 8 depicts an introduction cannula and stylet.
Figure 9:
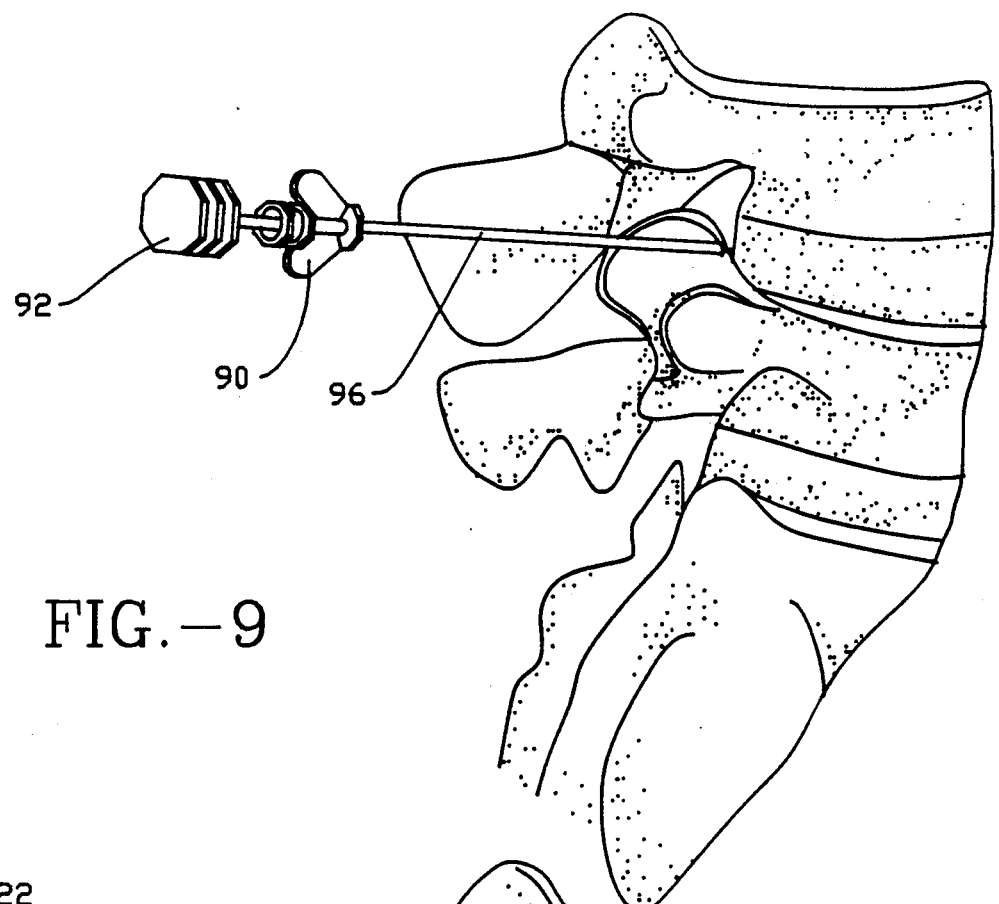
FIG. 9 shows the positioning of the cannula and stylet of FIG. 8 relative to an intervertebral disc.

The stylet 22 (FIGS. 3A, 3B) includes a solid shaft 80 with a pointed end 82 and a hub 84. The hub 84 includes first and second recesses 86, 88. The shaft 80 is insertable through the bore 52 of the needle body 26 such that the pointed end 82 projects out of the distal end 72 of the needle body 26. In this position, the hub 84 is rotatable so that the first and second recesses 86, 88 can lockingly engage the third and fourth tabs 58, 60 of the needle securing body 44. The stylet 22 acts in a traditional manner of assisting the introduction of the needle body 26 into the patient. In order to initially introduce the needle 20 and stylet 22 into the body, it is common medical procedure to first use an introduction cannula and stylet such as introduction cannula 90 and stylet 92 shown in FIGS. 8 and 9. The introduction cannula 90 includes a wing-shaped hub 94 which is secured to the cannula body 96. The cannula body 96 defines a central bore 98 which receives the shaft 100 of the stylet 92 with a pointed end 102 extending out of the cannula body 96. The stylet 92 includes a hub 104 which has recesses 106, which are removably lockable onto tabs 108 of the wing-shaped hub 94.

It is to be understood that the above described hubs can be injection molded using materials known in the trade.

It is to be understood that the o-ring 36 can be replaced by other devices for securing the needle body 26 onto the hub body 28. By example only, the projection 50 could alternatively cause a portion of the hub body 28 to become wedged against the needle body 26. Further, the projection 50 could itself be designed to become wedged between the needle body 26 and the hub body 28. Additionally, a compressible nose could be secured to the projection 50 and act much in the same way that the o-ring acts.

It is also to be understood that although the connector fins 38 are shown on hub body 28, that such fins or like devices could also be designed into the needle securing body 40 so that the needle securing body 40 could be selectively broken in order to released the hub body 28 from the needle body 26.

Industrial Applicability

The operation and procedure for use of the above instrumentation, is as follows.

Figure 10:
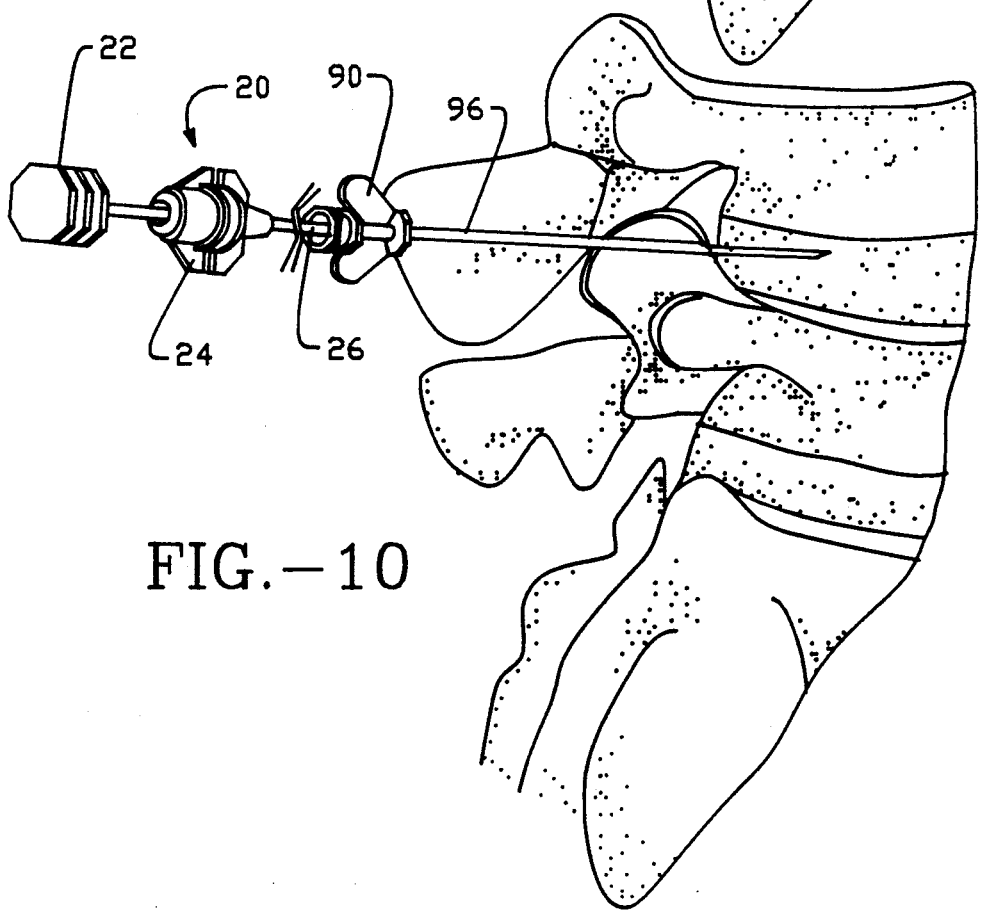
FIG. 10 depicts the surgical needle of FIG. 1 disposed through the cannula of FIG. 8.

After the surgical side is identified, the introduction cannula 90 with the stylet 92 locked into position thereon is inserted through the patient's skin and directed to the surgical site. Once it is verified that the cannula 90 has addressed the surgical site, the stylet 92 is removed by twisting the stylet 92 relative to the cannula 90 to unlock the stylet 92 from the cannula 90, and by pulling the stylet 92 back out of the cannula 90. After this has occurred, the surgical needle 20 with the stylet 22 lookingly secured therethrough is placed through the central bore 98 of the cannula 90 until the pointed end 82 projects through the cannula body 96 and is located at the surgical site. Then, the stylet 22 is twistingly unlocked from the tabs 58, 60 of the needle securing body 44 and removed from the surgical needle 20. At this point, radiological diagnostic fluids can be introduced through the needle 22 in order to diagnose the condition of the disc between two vertebral bodies (FIG. 10). If it occurs that other surgical procedures are indicated based on the radiological diagnosis, the hub 24 can be removed from the needle body 26 by a twisting action as described hereinabove and then the cannula 92 can be slid back over the needle body 26 and removed from the patient. After this is accomplished, the needle body 26 can be used as a trocar for the guidance and insertion of a larger dilator and cannula (not shown) over the needle body 26 in order to position the dilator and cannula adjacent the disc. Then, a surgical procedure to remove damaged herniated disc tissue can proceed as disclosed in the above two referenced U.S. patents.

It is to be understood that other embodiments of the present invention can be fashioned and fall within the spirit and scope of the appended claims.

Other objects and advantages of the invention can be obtained from a review of the figures and appended claims

I claim:

1. A surgical needle comprising:
   a needle body;
   a hub;
   said hub including means for securing said hub onto said needle body;
   said hub including non-reusable means for selectively releasing said securing means in order to allow said hub to be removed from said needle body, said non-reusable means for allowing the hub to be moved relative to and non-reconnectably released from, said needle body, said non-reusable means for not allowing said securing means to resecure said hub onto the needle body.

2. The surgical needle of claim 1 wherein:
   said securing means includes means for applying a compressive force to secure the needle body to the hub; and
   said securing means including means for compressing said applying means against said needle body and said hub to secure the needle body to said hub.

3. The surgical needle of claim 1 wherein:
   said non-reusable means for allowing the hub to be rotatably and non-reconnectably released from said needle body.

4. The surgical needle of claim 1 wherein said needle body has a longitudinal axis and wherein:
   said securing means includes means for securing said hub onto said needle when said securing means is urged in a direction along the longitudinal axis; and
   said non-reusable means for non-reusable releasing said securing means when said non-reusable means is rotated about the longitudinal axis.

* * * * *

UNITED STATES PATENT AND TRADEMARK OFFICE
CERTIFICATE OF CORRECTION

PATENT NO.   : 5,149,324
DATED        : September 22, 1992
INVENTOR(S)  : Benjamin S. Clawson It is certified that error appears in the above-identified patent and that said Letters Patent is hereby corrected as shown below:

Column 3, line 5, please delete "FIG. 1" and insert therefor --FIGS 1, 1A, 1B".

Column 3, line 23, please delete the word "looking" and insert therefor --locking--.

Column 3, line 29, please delete ", and projection 50".

Column 4, line 65, please delete the word "lookingly" and insert therefor --lockingly"

Signed and Sealed this

Ninth Day of November, 1993

Attest:

BRUCE LEHMAN

Attesting Officer

Commissioner of Patents and Trademarks